(12) United States Patent
Takekoshi

(10) Patent No.: US 7,683,909 B2
(45) Date of Patent: Mar. 23, 2010

(54) IMAGE MANAGEMENT DEVICE AND METHOD FOR MANAGING PLURALITY OF IMAGES

(75) Inventor: Koji Takekoshi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 990 days.

(21) Appl. No.: 11/174,804

(22) Filed: Jul. 5, 2005

(65) Prior Publication Data

US 2006/0008181 A1 Jan. 12, 2006

(30) Foreign Application Priority Data

Jul. 7, 2004 (JP) ............................. 2004-200920

(51) Int. Cl.
 G06T 17/00 (2006.01)
 G09G 5/00 (2006.01)
 G06K 9/00 (2006.01)

(52) U.S. Cl. ........................ 345/581; 345/424; 382/132

(58) Field of Classification Search ................ 345/420, 345/581, 606, 804, 418, 20, 424; 348/207.1; 382/128, 224, 305, 324, 132, 159; 707/104.1
See application file for complete search history.

(56) References Cited

U.S. PATENT DOCUMENTS

| | | | | |
|---|---|---|---|---|
| 5,586,239 | A * | 12/1996 | Ueda | 715/513 |
| 6,008,812 | A * | 12/1999 | Ueda et al. | 345/418 |
| 6,030,116 | A * | 2/2000 | Yanai et al. | 374/142 |
| 6,256,042 | B1 * | 7/2001 | Iga | 345/619 |
| 6,832,101 | B1 * | 12/2004 | Kino | 455/550.1 |
| 7,076,118 | B1 * | 7/2006 | Westerman | 382/305 |
| 2001/0010732 | A1 * | 8/2001 | Oosawa | 382/128 |
| 2003/0030637 | A1 * | 2/2003 | Grinstein et al. | 345/420 |
| 2003/0035584 | A1 | 2/2003 | Nicholas et al. | |
| 2003/0142859 | A1 * | 7/2003 | Okuzawa | 382/132 |
| 2003/0184653 | A1 * | 10/2003 | Ohkubo | 348/207.1 |

(Continued)

FOREIGN PATENT DOCUMENTS

EP 0 915 427 A2 5/1999

(Continued)

OTHER PUBLICATIONS

Notification of First Office Action, dated Jul. 20, 2007, in the counterpart Chinese Patent Application 2005100829345 (Chinese and English translation).

*Primary Examiner*—Amare Mengistu
*Assistant Examiner*—Aaron M Guertin
(74) *Attorney, Agent, or Firm*—Cowan, Liebowitz & Latman, P.C.

(57) ABSTRACT

The present invention provides an image management device and an image management method, both capable of easily performing comparison and reference of images in which taken images and processed images generated from the taken images are intermingled. For that purpose, based on the discrimination results of the attributes of the images by an attribute discrimination unit, an image classification unit classifies the processed images in order that the processed images may be mutually associated or processed images may be associated with taken images related to the processed images. A classified image list is displayed by an image list display unit, and images selected from the list are displayed on an image display unit. Furthermore, the image list displayed on the image list display unit is changed by classification switching by an image classification switching unit.

9 Claims, 17 Drawing Sheets

U.S. PATENT DOCUMENTS

2003/0193502 A1 * 10/2003 Patel et al. .................. 345/440

FOREIGN PATENT DOCUMENTS

| JP | 2001-218110 | 8/2001 |
| JP | 2003-126046 | 5/2003 |
| JP | 2003-196300 | 7/2003 |
| JP | 2003-284691 | 10/2003 |

* cited by examiner

FIG. 7

PATIENT/STUDY LIST 706

| PATIENT ID | PATIENT NAME | MODALITY | TEST DATE | TEST TIME |
|---|---|---|---|---|
| 001 | NAME | SC | 2003.12.26 | 12:10:32 |
| 001 | NAME | CR | 2003.12.26 | 11:38:56 |
| 001 | NAME | SC | 2002.05.11 | 16:42:19 |
| 001 | NAME | CR | 2002.05.11 | 16:31:05 |
| 001 | NAME | CR | 2001.01.15 | 09:50:39 |

PATIENT/STUDY LIST 904

| PATIENT ID | PATIENT NAME | MODALITY | TEST DATE | TEST TIME |
|---|---|---|---|---|
| 001 | NAME | CR | 2003.12.26 | 11:38:56 |
| 001 | NAME | CR | 2002.05.11 | 16:31:05 |
| 001 | NAME | CR | 2001.01.15 | 09:50:39 |

PATIENT/STUDY LIST 1105

| PATIENT ID | PATIENT NAME | MODALITY | TEST DATE | TEST TIME |
|---|---|---|---|---|
| 001 | NAME | CR | 2003.12.26 | 11:38:56 |
| 001 | NAME | CR | 2002.05.11 | 16:31:05 |
| 001 | NAME | CR | 2001.01.15 | 09:50:39 |
| 001 | NAME | SC | 2003.12.26 | 12:10:32 |

1104
1103
1102
1101

IMAGE MANAGEMENT DEVICE AND METHOD FOR MANAGING PLURALITY OF IMAGES

BACKGROUND OF THE INVENTION

1. Field of the Invention

The present invention generally relates to an image management device and an image management method, and more particularly to an image management device and an image management method, both managing taken images radiographed as medical images and processed images created from the taken images.

2. Related Background Art

Conventionally, in a medical field, various modalities such as an X-ray radiographing device, a computer tomography (CT) device, a magnetic resonance imaging (MRI) device and a computed radiography (CR), which use radiations such as an X-ray, are used for a diagnosis.

These digital images are stored in a format in conformity with a standard generally called as digital imaging and communication in medicine (DICOM). The format is configured as a hierarchical structure. A layer of test is located at the uppermost hierarchy. A layer of series is located under the test, and a layer of image is located under the series.

Because these layers are considered based on radiographing, the test is located at the uppermost layer. Consequently, when DICOM images are searched from a database (DB) to be displayed as a list, the list of test, which is located at the uppermost layer, is generally displayed.

Moreover, each digital image is classified into classes by its modality. For example, a CT image is classified into a CT class, and a CR image is classified into a CR class. To put it more concretely, for example in the case of the CT class, ID indicating the CT class is recorded at an image header.

On the other hand, a new digital image can be created by performing image processing of a digital image. Such a newly created image is classified into a class called as a secondary capture (SC).

On the other hand, in X-ray radiographing aiming at a medical diagnosis, a film screen system combining an intensifying screen with an X-ray radiographing film has been used. In a radiographing method using the system, X-rays having passed a subject include the internal information of the subject, and the X-rays are converted into visible light in proportion to the intensities of the X-rays. Then, the X-ray radiographing film is exposed by the visible light, and an X-ray image is formed on the film.

Conventionally, when a diagnosis is performed with such a film, in order to judge the progress of a disease and the progress of curing, the diagnosis has been performed by arranging two images radiographed with an interval with time on a Schaukasten or the like to compare both the images.

On the other hand, in the field of orthopedic surgery or the like, in order to radiograph a big subject which is too large to be radiographed by one-shot, a plurality of times of X-ray radiographing is performed, and a diagnosis and a measurement are performed by joining a plurality of the radiographed films to one another.

For example, it is necessary for a diagnosis of scoliosis to radiograph the overall view of the backbone, and there is a case where the subject is larger than the size of a radiographing device to make it impossible to radiograph the subject by one-shot. In such a case, the radiographing is performed over two times, and the created two sheets of X-ray films are physically glued together with an adhesive tape or the like for the judgment of symptoms.

On the other hand, an X-ray digital radiographing device has been begun to be used recently which composes a digital image by reading a radiation image as an electric signal by various systems and converting the electric signal into a digital signal, which systems are a system of reading an X-ray intensity distribution after forming the X-ray intensity distribution as a latent image of energy in a stimulable phosphor, a system of reading the fluorescence distribution of phosphor by X-rays directly, a system of not using any fluorescence distribution, and the like.

Thereby, because the radiographed image can be taken in as digital data, it has become possible to acquire a difference between pieces of digital data acquired with a time interval by image processing. Consequently, the progressing situation or the curing situation of a disease is conventionally judged by a human head by comparing two images arranged on a Schaukasten or the like with each other.

In recent years, as described above, because it has become possible to perform X-ray digital radiographing to acquire image data as digital data, by displaying a difference image acquired by operating the difference between two X-ray images on a monitor or the like as a reference image, the clear proceeding of curing or the progressing of a disease is shown by referring to the difference image by the digital image processing without judging changes of the progressing situation or the curing situation of an affected area by the comparison with a past image as described above. Consequently, the presentation of a difference image is very effective means for supporting the judgment of a doctor.

On the other hand, also in the field of the orthopedic surgery, similarly it has become possible to handle image data as digital data. Consequently, although two images have been joined to each other by gluing them physically with an adhesive tape or the like until now, it has become possible to perform a diagnosis by joining two images to each other more easily and more accurately by digital image processing. Consequently, a subject measured by gluing two films physically in the prior art has become possible to be measured in a moment on a monitor, and then the X-ray digital radiographing has become effective means for decreasing the workloads of a doctor.

Here, there is a method of storing the history of image processing as prior art of the method of displaying images processed in the past (for example, Japanese Patent Application Laid-Open No. 2003-284691).

Moreover, there is also a method of creating incidental information including the information indicating the storage place of image data (for example, Japanese Patent Application Laid-Open No. 2003-196300).

Moreover, a compression/registration combining technique for implementing a time subtraction as an application service provider for detecting variations of medical imaging with time is also disclosed (for example, Japanese Patent Application Laid-Open No. 2003-126046 (corresponding to United States Patent Published Application No. 2003-35584)).

Furthermore, also an image display device enabling an easy search and the like by making each image be accompanied by history information such as the information on whether an operation between images has been performed or not, and the information for specifying the images used as the basis of the operation between the images when the operation between the images has been performed is disclosed (for example, Japanese Patent Application Laid-Open No. 2001-218110 (corresponding to United States Patent Published Application No. 2001-10732)).

SUMMARY OF THE INVENTION

However, in any of the prior art, when images in a plurality of classes are tried to be displayed in the order of test date, the images are displayed in a state in which the images in the plurality of classes are mixed, and consideration on a diagnosis is disturbed, so that the diagnosis becomes very troublesome one. When the images in the plurality of classes are tried to be displayed by every class lest the images in the plurality of classes should be simultaneously displayed for avoiding the problem, there is conversely another problem that the images in the other classes cannot be referred to.

It is an object of the invention of the present application to provide an image management device and an image management method, both capable of easily performing the comparison and the reference of the images in a radiographed modality class and the images in a secondary capture class, which have been generated from the taken images, by changing the association of the images in various modality classes.

The inventor of the invention of the present application thought of the several aspects of the invention shown below as a result of repeating examinations wholeheartedly in order to settle the problems mentioned above.

An image management device according to the invention of the present application includes an attribute judgment unit judging whether an image is a processed image generated by performing image processing of a taken image or whether the image is a taken image based on attribute information of the image, a classification unit classifying the image based on a judgment result of the attribute judgment unit pertaining to whether the image is the taken image or the processed image, an image list display unit displaying an image list based on a classification result of a classification by the classification unit, and an image display unit displaying an image selected from the image list displayed by the image list display unit.

Moreover, an image management method of the invention of the present application includes an attribute judgment step of judging whether an image is a processed image generated by performing image processing of a taken image or whether the image is a taken image based on attribute information of the image, a classification step of classifying the image based on a judgment result at the attribute judgment step pertaining to whether the image is the taken image or the processed image, an image list display step of displaying an image list based on a classification result of a classification at the classification step, and an image display step of displaying an image selected from the image list displayed at the image list display step.

BRIEF DESCRIPTION OF THE DRAWINGS

FIG. 7 is a view showing an example of displaying the images shown in FIG. 6 on a display screen as an image list;

FIG. 9 is a view showing an example of displaying the images shown in FIG. 8 on the display screen as an image list;

FIG. 11 is a view showing an example of displaying the images shown in FIG. 10 on the display screen as an image list;

DETAILED DESCRIPTION OF THE PREFERRED EMBODIMENTS

Hereinafter, the preferred embodiments of the invention of the present application are concretely described with reference to the attached drawings.

First Embodiment

Figure 1:
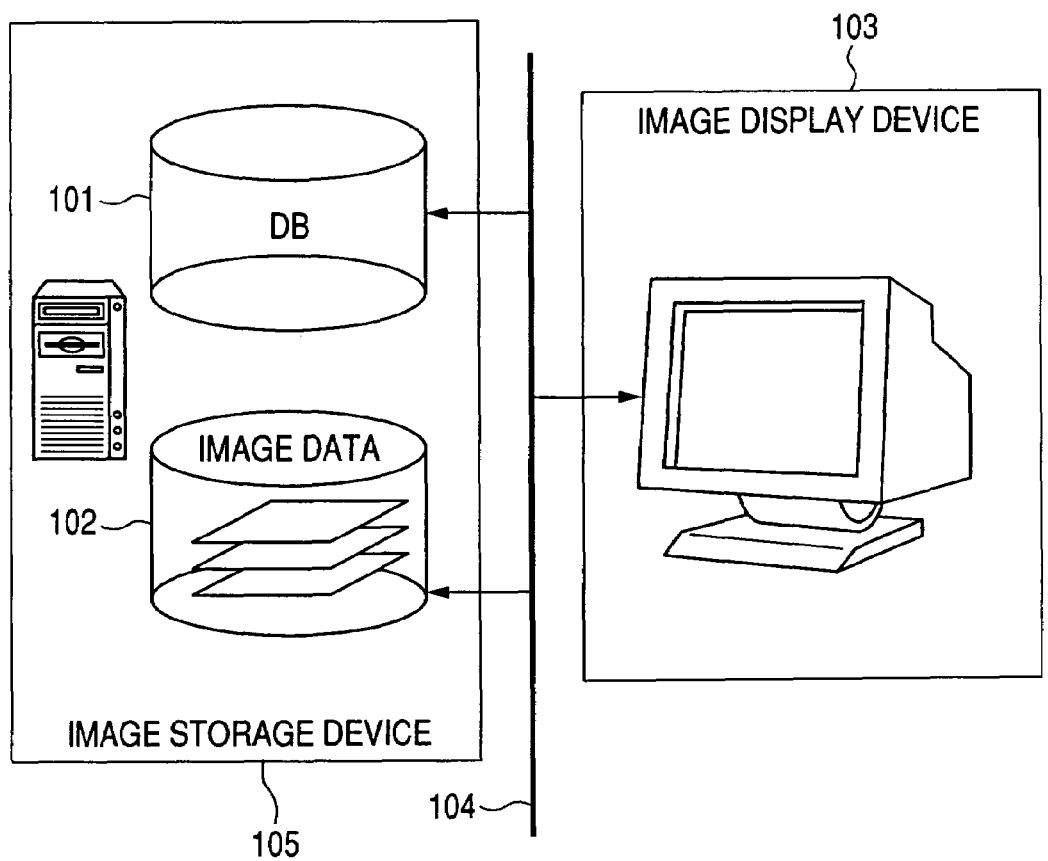
FIG. 1 is a view showing the configuration of an image management device according to an embodiment of the present invention.

FIG. 1 is a view showing the configuration of an image management device according to an embodiment of the present invention.

In the image management device, an image storage device 105, storing patient information and image data, and an image display device 103 are mutually connected by a network 104. The image storage device 105 is provided with a database 101, storing attribute information such as patient information, and a storage medium 102, storing image data associated with the attribute information stored in the database 101.

Moreover, the image storage device 105 is provided with not shown general components of a computer such as a CPU and a ROM. A program for the CPU to control the operation of the whole image storage device 105 is stored in the ROM.

Similarly, the image display device 103 is provided with not shown general components of a computer such as a CPU and a ROM. A program for the CPU to control the operation of the whole image display device 103 is stored in the ROM.

Incidentally, although the image storage device 105 and the image display device 103 are configured to be computers separated from each other in the present embodiment, these computers may be integrated to be one body.

Figure 2:
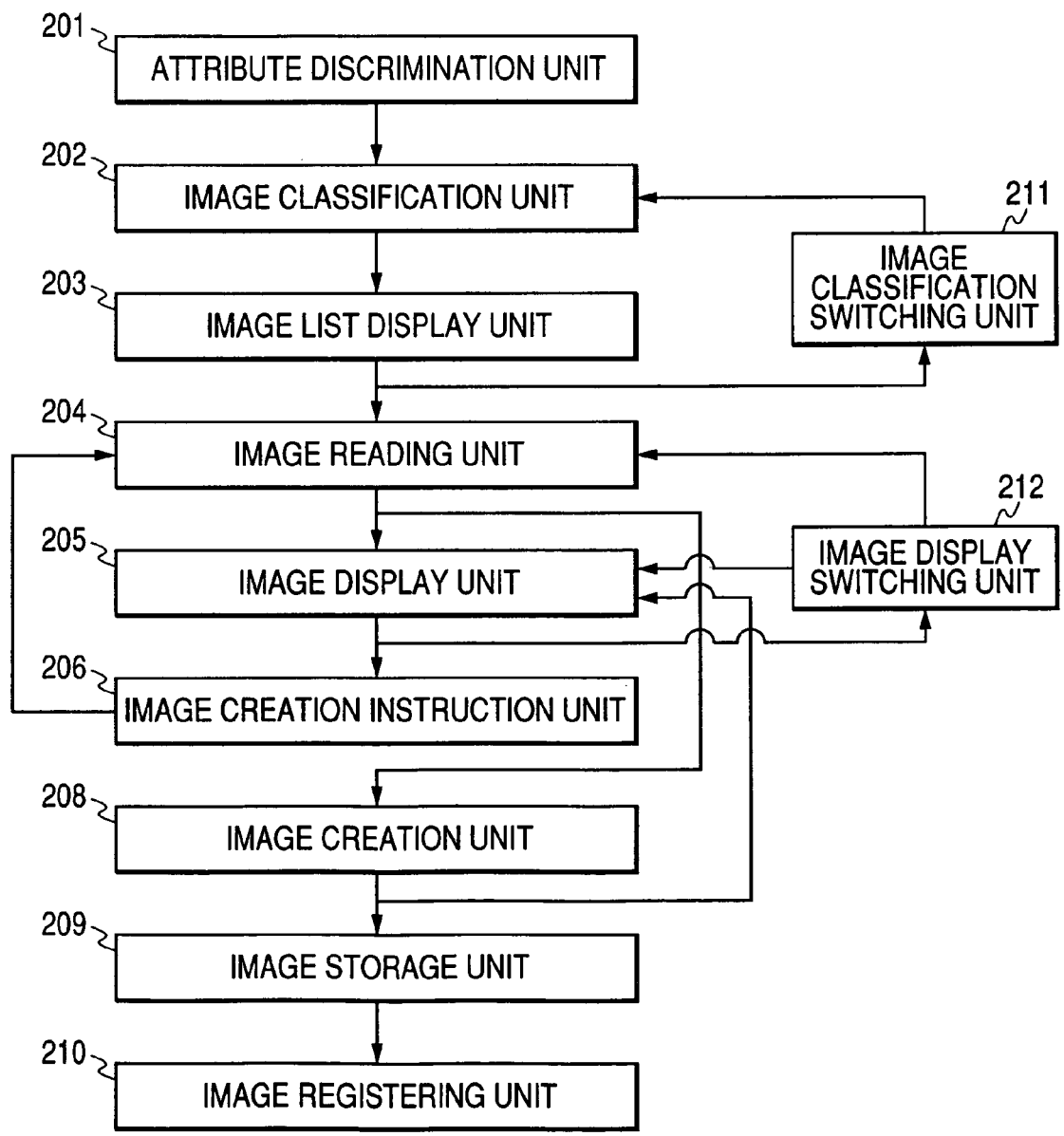
FIG. 2 is a functional block diagram showing the functions of the image management device according to the embodiment of the present invention.

FIG. 2 is a functional block diagram showing the functions of the image management device according to the embodiment of the present invention.

In the image management device, each unit shown in FIG. 2 is configured by the CPU's execution of the programs or the like stored in the ROM's in the image display device 103 and the image storage device 105.

That is, the image management device is provided with an attribute discrimination unit 201, which discriminates image attributes, an image classification unit 202, which classifies images based on a result of the discrimination of the attribute discrimination unit 201, an image list display unit 203, which displays an image list based on a result of the classification by the image classification unit 202, an image reading unit 204, which reads images selected from the image list displayed by the image list display unit 203, and an image display unit 205, which displays the images read by the image reading unit 204.

Furthermore, the image management device is provided with an image creation instruction unit 206, which gives an instruction of creating images from the images displayed on the image display unit 205, an image creation unit 208, which newly creates images from the images read by the image reading unit 204, an image storage unit 209, which stores the images created by the image creation unit 208, an image registering unit 210, which registers the images stored by the image storage unit 209, an image classification switching unit 211, which switches the method of the classification by the image classification unit 202, and an image display switching unit 212, which switches the order of the arrangement of the images displayed on the image display unit 205.

The image reading unit 204 also performs the operation of reading the images, if the images instructed by the image creation instruction unit 206 have not been read.

Figure 3A:
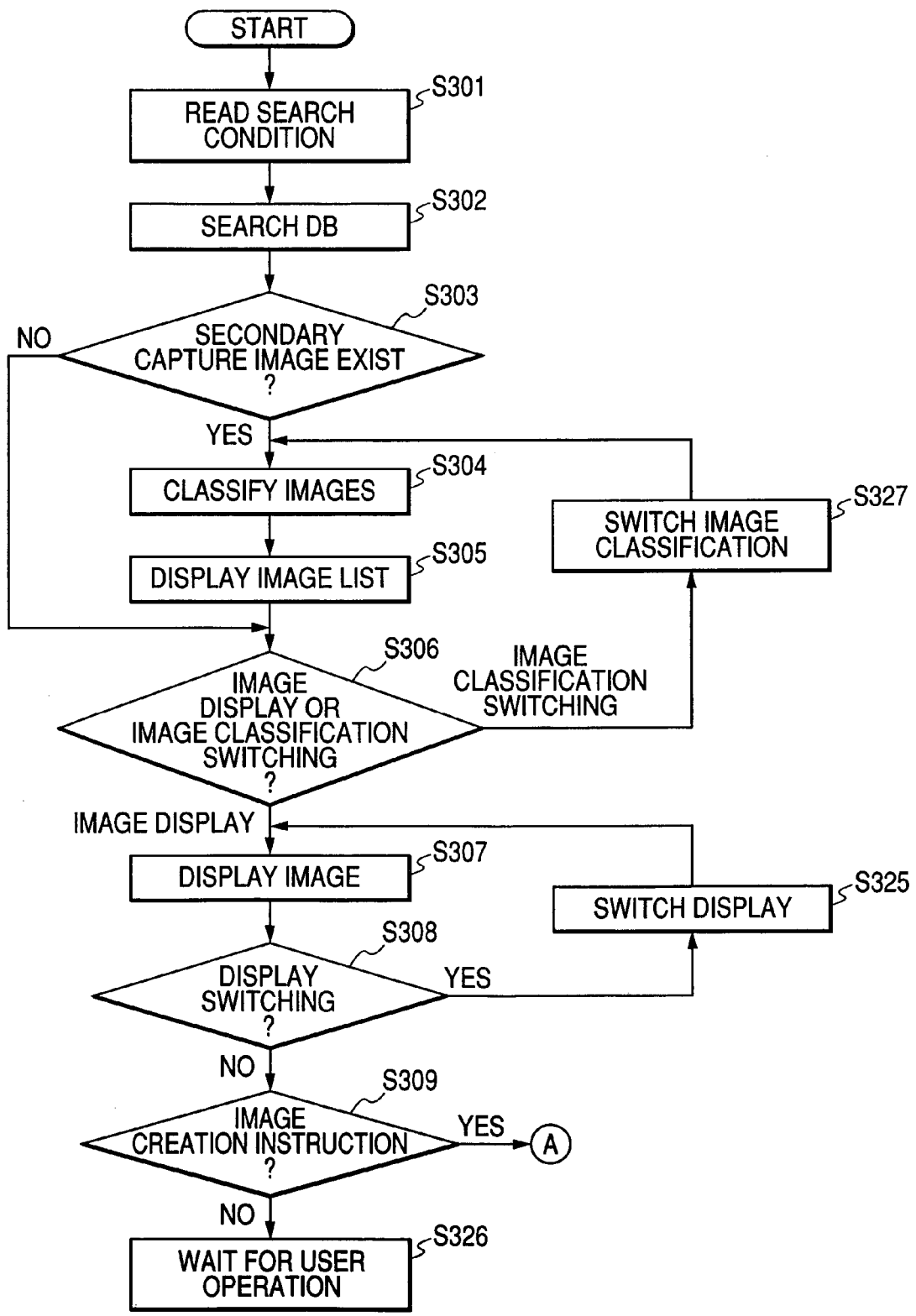
FIG. 3A is a flowchart showing a processing operation of the image management device according to the embodiment of the present invention.
Figure 3B:
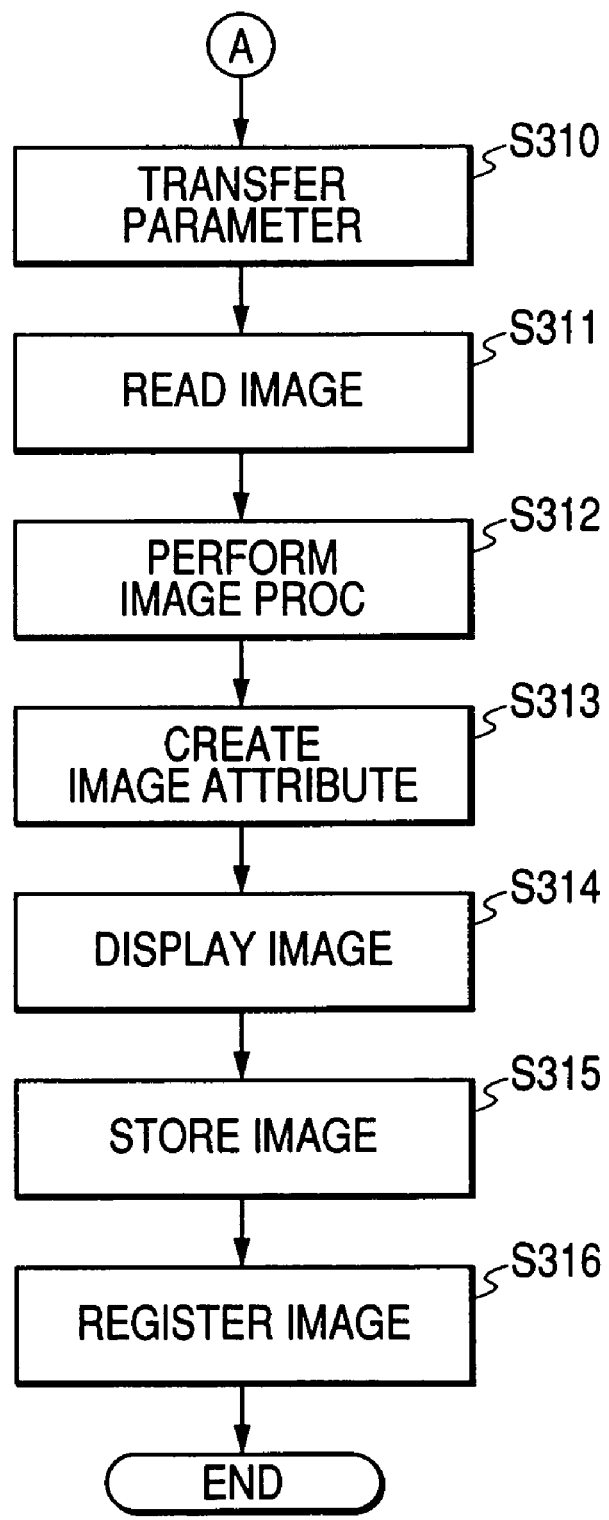
FIG. 3B is a flowchart showing the processing operation of the image management device according to the embodiment of the present invention following on FIG. 3A.

Next, the operation of the image management device configured as described above is described. FIGS. 3A and 3B are flowcharts illustrating the processing operation of the image management device according to the embodiment of the present invention.

First, search conditions are inputted from the input device (not shown) of the image display device 103 or the like based on an operation of a user (Step S301). As the items of the search conditions, for example, a test day, a patient ID, a patient name, a class attribute, a sex, a birth date and the like can be cited.

Next, the image management device searches the database 101 in accordance with the inputted search conditions (Step S302).

Subsequently, the attribute discrimination unit 201 discriminates whether any secondary capture images exist in the searched images at Step S302 or not (Step S303).

There are two kinds of discrimination methods as the discrimination method at Step S303. One of them discriminates whether any secondary capture class images exist in the searched images or not, and the other of them discriminates whether any secondary capture class images related to the searched images are registered in the DB 101 or not. It depends on the setting of the user that at Step S303 which discrimination method of the two discrimination methods is used, both of the discrimination methods are executed, or any of the discrimination methods are not used.

When it is discriminated at Step S303 that some secondary capture images exist, the image classification unit 202 executes image classification (Step S304). Usually, the images of the same patient are classified as the same group. Furthermore, the image management device executes the classifications of the search results at Step S302 and the images in the secondary capture class related to the searched images.

The classification method is as follows. That is, one of them is a classification method of performing the classification by associating the images in the secondary capture class with the original images at the creation of them. Another method is a classification method of classifying the images of the secondary capture class collectively into one group. Alternatively, further method is a classification method of handling the images in the secondary capture class independently without associating with any images.

Figure 4:
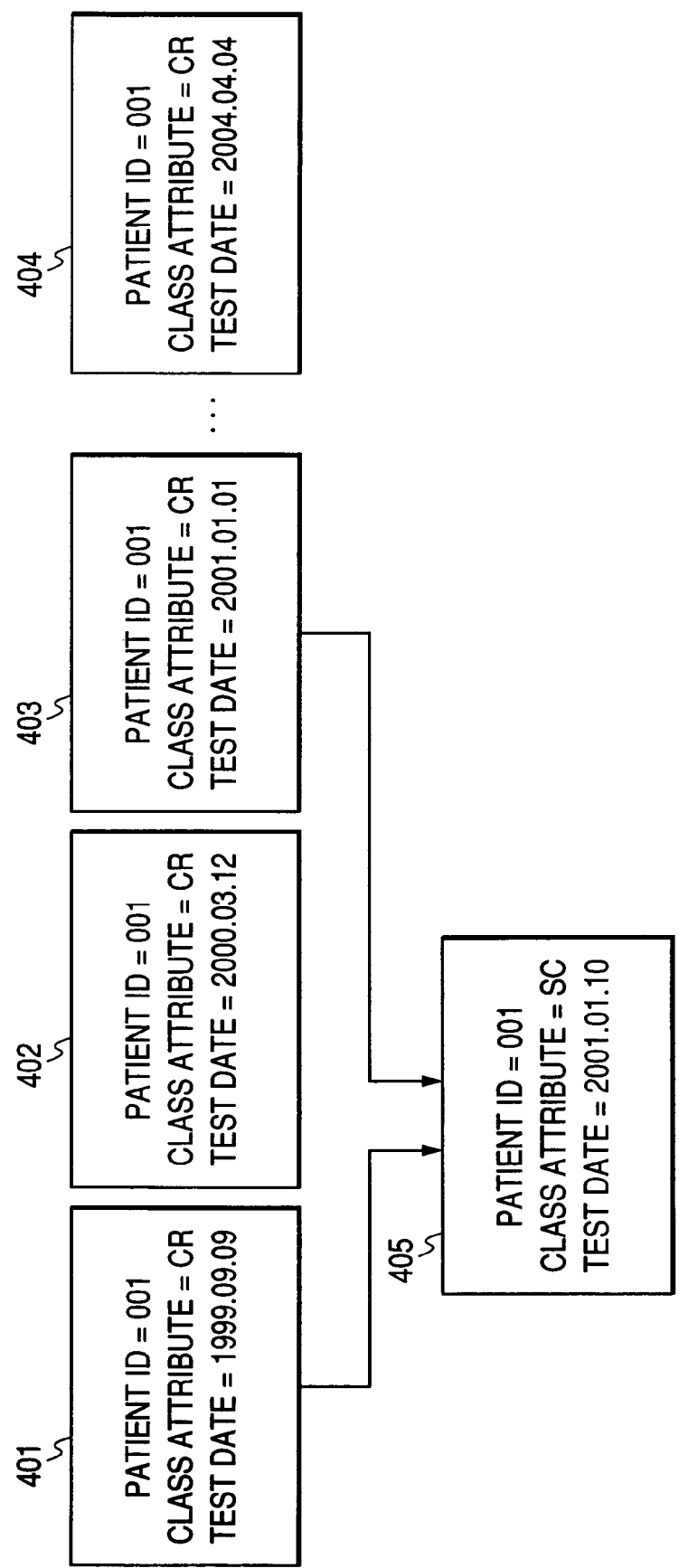
FIG. 4 is a view showing the relations between images of a CR class and an image of a secondary capture class.

Here, a concrete example of the search is described using FIG. 4. In FIG. 4, it is supposed that the pieces of attribute information 401-405 are stored in the database 101, and that the image data corresponding to each of the pieces of the attribute information 401-405 are stored in the storage medium 102. (Incidentally, in the following, the image data corresponding to attribute information A is simply referred to as image A.) For example, when images are searched under the search conditions of "patient ID is No. 001", and of "test date is within a range of from Jan. 1, 1999 to Dec. 31, 2001", images 401, 402, 403 and 405 are searched in the example shown in FIG. 4.

The image 405 of the secondary capture class is included in the searched images (a mark SC shows the secondary capture class). In this example, the image 405 is supposed to be generated from the images 401 and 403. Then, an image classification is executed after that. The details of the image classification will be described later.

On the other hand, as an example of different search conditions, for example, when "the patient ID is No. 001", and "the image of CR class" are searched, the images 401, 402, 403 and 404 are searched in the example shown in FIG. 4.

Although the image (the image 405 in the example of FIG. 4) of the secondary capture class does not exist in the searched images, the image 405 of the secondary capture class relevant to the images 401 and 403 is registered in the DB 101. Accordingly, the image classification about the images 401, 402, 403, 404 and 405 is performed. The details of the image classification will be described later.

Before describing the details of the image classification, the DICOM format is described briefly here.

Figure 5:
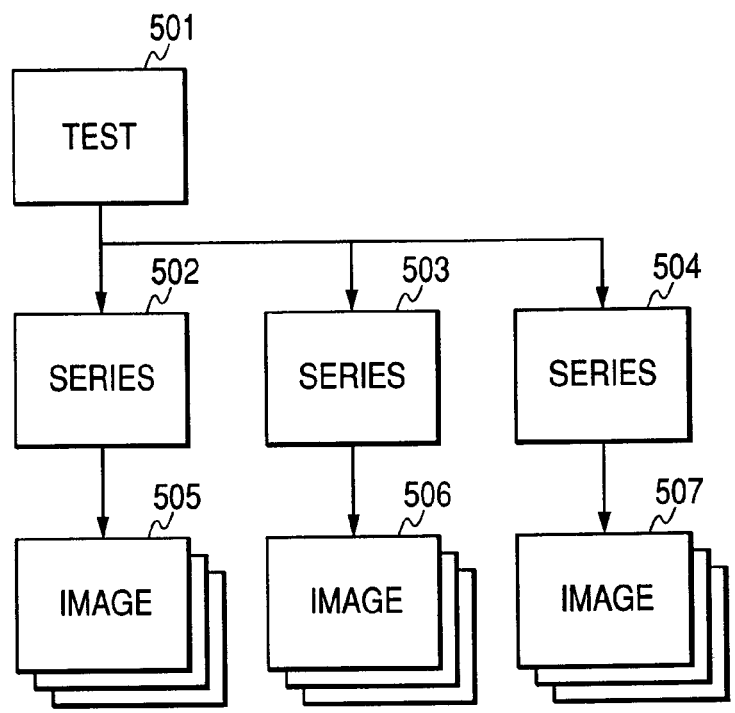
FIG. 5 is a view showing a hierarchical structure of the image attribute regulated by the DICOM standard.

FIG. 5 is a view showing the hierarchical structure of the image attributes regulated by the DICOM standard.

The hierarchical structure consists of three layers, and a layer 501 of test is located in the uppermost hierarchy. Layers 502-504 of series are located under the layer 501 of the test, and the layer 501 of the test can have one or more layers of the series. Under the layers 502-504 of series, layers 505-507 of images are located, respectively. Each of the layers 502-504 of series can have one or more layers of images. Here, the information specifying patient information is, for example, the attribute information stored at the layer 501 of test.

Moreover, as the examples of the generation of an image of the secondary capture class, there can be cited one which is an elapsed difference image acquired by obtaining the difference between the images belonging to different tests performed with an interval of time, one which is a digital image newly generated by joining two or more images in the same test together to be one image, one which is an image as a result of image processing such as a tone correction of a radiographed image, which processed image is stored as new image data, one which is a digital image acquired by scanning a medical image of a film with a medical film scanner or the like, and the like. Because these images are generated using a well-known technique, their details are omitted.

Next, the classification method of images is described by exemplifying a case where elapsed difference images are generated as the secondary capture class.

Figure 6:
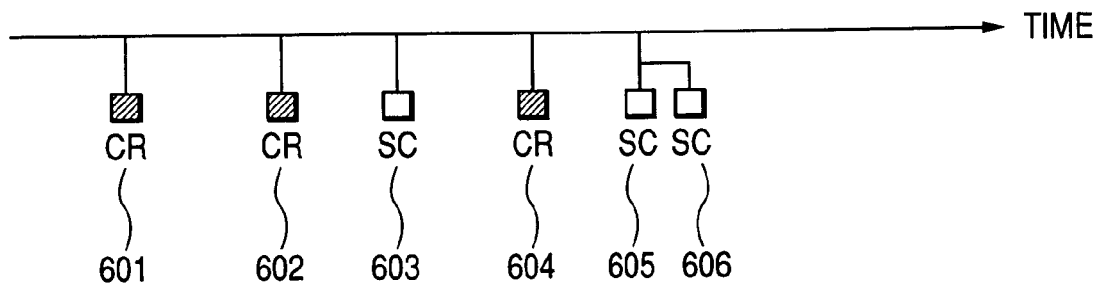
FIG. 6 is a conceptual diagram showing the relation of generated images.

For example, as shown in FIG. 6, after the radiographing of images 601 and 602 of the CR class is performed, an elapsed difference image of the images 601 and 602 is created, and then the creation of an image 603 in the secondary capture class is performed. After that, when the radiographing of an image 604 is performed and elapsed difference images of the images 604 and 601 and the images 604 and 602 are created, images 605 and 606 in the secondary capture class are generated.

Although the images 605 and 606 are created as the images belonging to the same test in the present embodiment here, the present invention is not limited to such a case. The images 605 and 606 may be separately created as different tests.

A case where the classification of these images is performed is described.

Figure 8:
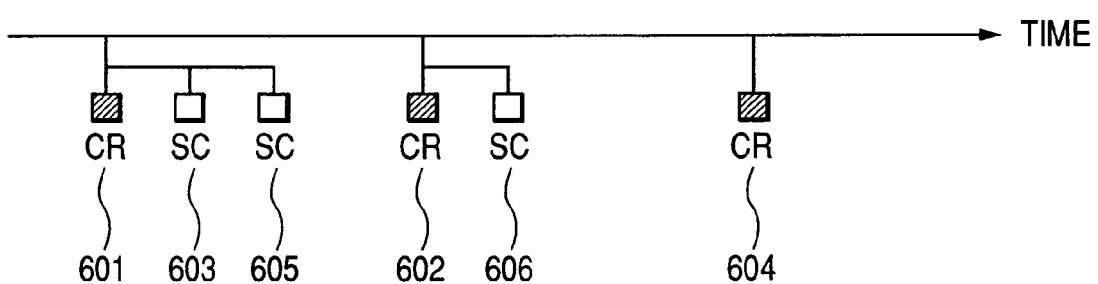
FIG. 8 is a conceptual diagram when the images shown in FIG. 6 are classified.

In the case where the classification is performed by the method of classifying the images of the secondary capture class by associating the images with the original images from which the images of the secondary capture class have been generated, the images created in the way shown in FIG. 6 are classified in the way shown in FIG. 8.

Since the image 603 is an image generated from the images 601 and 602, the image 603 is classified as the test same as that of the image 601, which is the image generation origin. Similarly, the images 605 and 606 are also classified as the images of the tests to which the images 601 and 602, being the image generation origins, severally belong, respectively.

Figure 10:
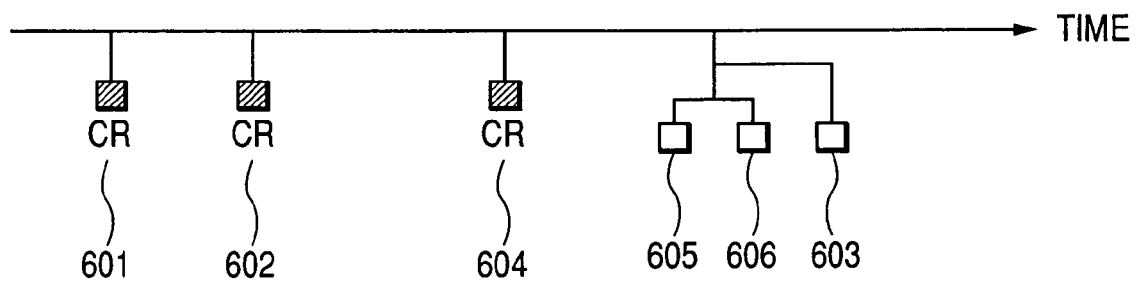
FIG. 10 is another conceptual diagram when the images shown in FIG. 6 are classified.

In the case where the images are classified by the method of classifying the images of the secondary capture class collectively to one, the images having been created in the way shown in FIG. 6 are classified in the way shown in FIG. 10.

Since the images 603, 605 and 606 are the images of the secondary capture class, they are collected as one test.

Incidentally, a classification of the images in the test of the secondary capture class may be performed so that the image 603 is classified to one series and the images 605 and 606 are classified to one series.

After the image classification unit 202 has classified the images in the way described above, the image list display unit 203 displays the image information classified at Step S304 as an image list (Step S305).

For example, when the images shown in FIG. 6 are displayed in the order of test dates without performing the classification by the class attributes at Step S304, an image list is displayed as shown in FIG. 7. Because the classification by the class attributes is not performed, the images of the CR class and the images of the secondary class are mixed to be displayed in the order of test dates in the image list 706.

Hereupon, items 701, 702 and 704 indicate the images 601, 602 and 604, respectively. Moreover, an item 703 indicates the image 603 of the secondary capture class, which has been generated by the images 601 and 602, and an item 705 indicates the images 605 and 606 of the secondary capture class, which have been generated from the image 604 and the images 601 and 602, respectively. In this display example, since the images 605 and 606 are collected as one test, they are displayed as one item also on the list.

On the other hand, in the case where the images are classified in the way of associating the images of the secondary capture class with the images from which the images of the secondary capture class have been generated, the images shown in FIG. 6 are classified in the way shown in FIG. 8.

A result of the list display of the images classified in such a way is displayed as a list 904 of FIG. 9. Although an item 901 is displayed by one line as one test, the images 601, 603 and 605 are classified as the images indicated by the item 901. An item 902 indicates the classified images 602 and 606, and an item 903 indicates the classified image 604.

Incidentally, although the secondary capture images are associated with the old test sides of the test dates of the images from which the secondary capture images have been generated, the secondary capture images may be associated with the new test sides.

On the other hand, when the images of the secondary capture class are collectively classified to one, the images shown in FIG. 6 are classified in the way shown in FIG. 10. A result of the list display of the images classified in such a way is displayed as a list 1105 of FIG. 11. An item 1101 indicates the images of the secondary capture class, which are collected to be one. That is, the item 1101 indicates the classified images 603, 605 and 606.

Incidentally, although the list display is performed in the order of the test dates here and the item 1101 is displayed at the end of the list since the test indicated by the item 1101 has been classified to the secondary capture class, the item 1101 may be displayed in accordance with the order of the test dates.

Subsequently, the image management device judges whether an image display is performed or whether the switching of an image classification is performed (Step S306). This judgment is performed by judging whether the user has inputted an image display instruction or a switching instruction of the image classification using an input device.

When the switching of the image classification is instructed by the user, the image classification switching unit 211 performs the switching of the image classification (Step S327). The switching of the image classification switches the classification method of the images classified at Step S304. That is, the switching switches whether the images of the secondary capture class are classified in the way of associating the images with the images from which the images of the secondary capture class have been generated, whether the images of the secondary capture class are classified in the way of collecting them to one, or whether the images of the secondary capture class are handled without being associated with any images.

For example, if the images shown in FIG. 6 are not associated with the images of the secondary capture class when the images shown in FIG. 6 exist, the images of the secondary capture class are handled as independent tests. Consequently, the images are classified as shown in FIG. 7. Moreover, when the images are classified in the way of associating the images of the secondary capture class with the images from which the images of the secondary capture class have been generated, the classification is performed as shown in FIG. 8. When their list display is executed, the list display is displayed as shown in FIG. 9.

Moreover, when the images of the secondary capture class are collectively classified into one, the classification is performed as shown in FIG. 10. When a list display is executed, the list display is performed as shown in FIG. 11.

When an image display is instructed by the user, the image display unit 205 excuses the display of images at Step S307.

Figure 12:
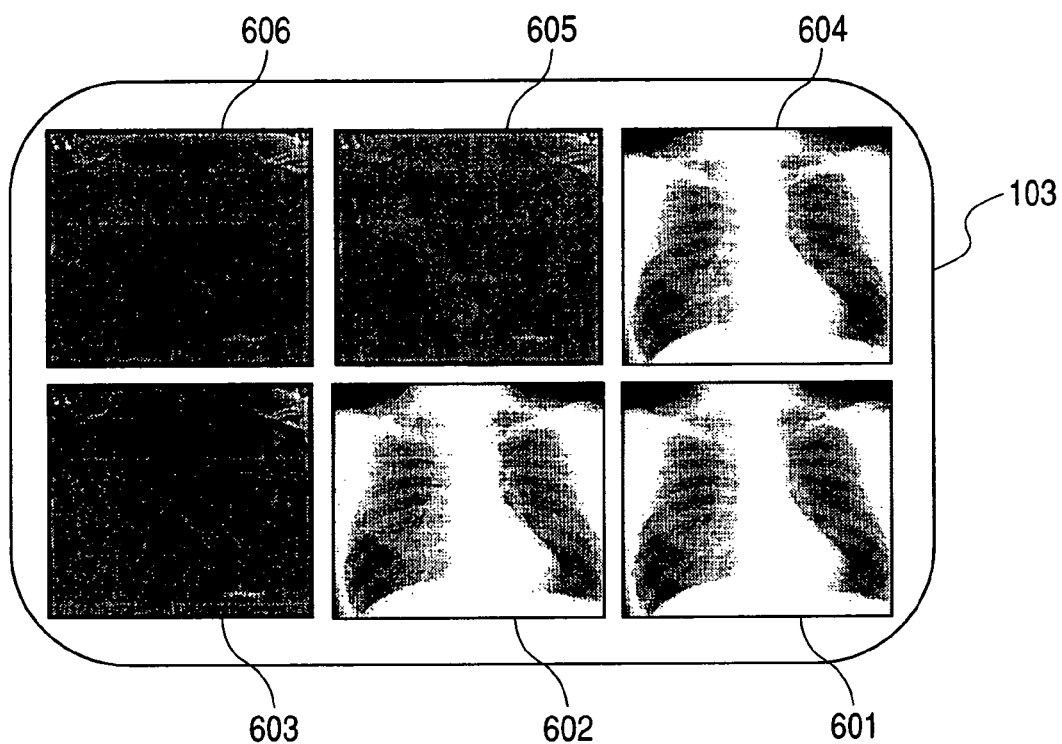
FIG. 12 is a view showing an example of displaying the images shown in FIG. 6 on the display screen.

For example, if the association of the images shown in FIG. 6 with the images of the secondary class is not performed, the taken images and the secondary capture images are mixed to be displayed as shown in FIG. 12.

Although the images are displayed from the upper left side to the upper right side and from the lower left side to the lower right side in the order of the newer test date to the older test date in this example, the display order of the images is not limited to this order.

Figure 13:
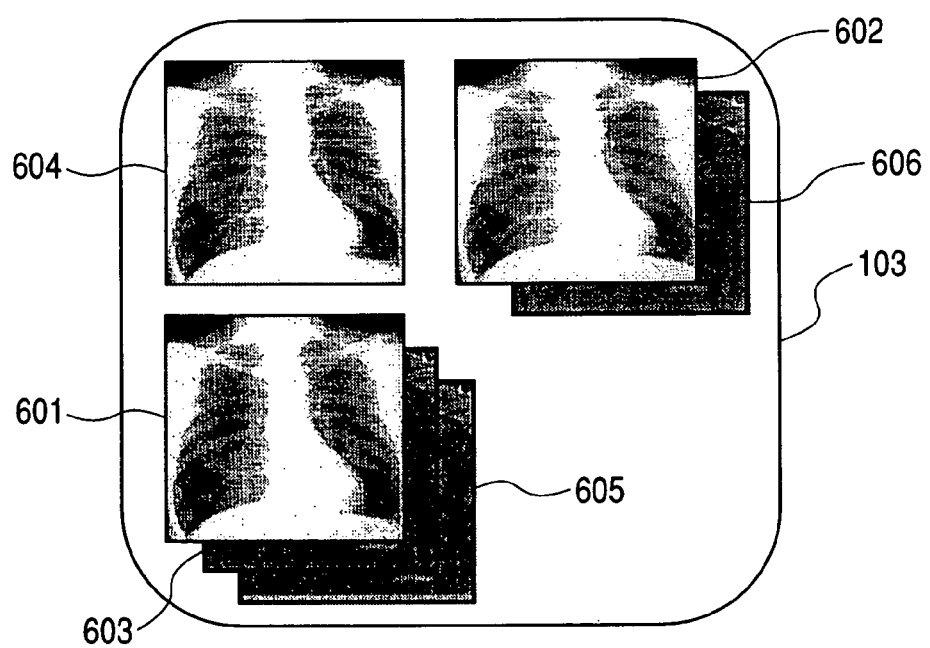
FIG. 13 is a view showing an example of displaying the images shown in FIG. 8 on the display screen.

Moreover, if the classification of the images shown in FIG. 6 is performed in the way of associating the images of the secondary capture class with the images from which the images of the secondary capture class have been generated, the images are displayed as shown in FIG. 13.

Hereupon, the image 602 has the associated image 606 of the secondary capture class, and the image 601 similarly has the associated images 603 and 605 of the secondary capture class.

These associated images are shown in the way of being hidden behind the respective CR images for description, but the associated images are not displayed normally. When the user instructs the display of the secondary capture images with the input device or the like, the associated images are switched from the images of the CR class to be displayed. The details thereof will be described later.

Figure 14:
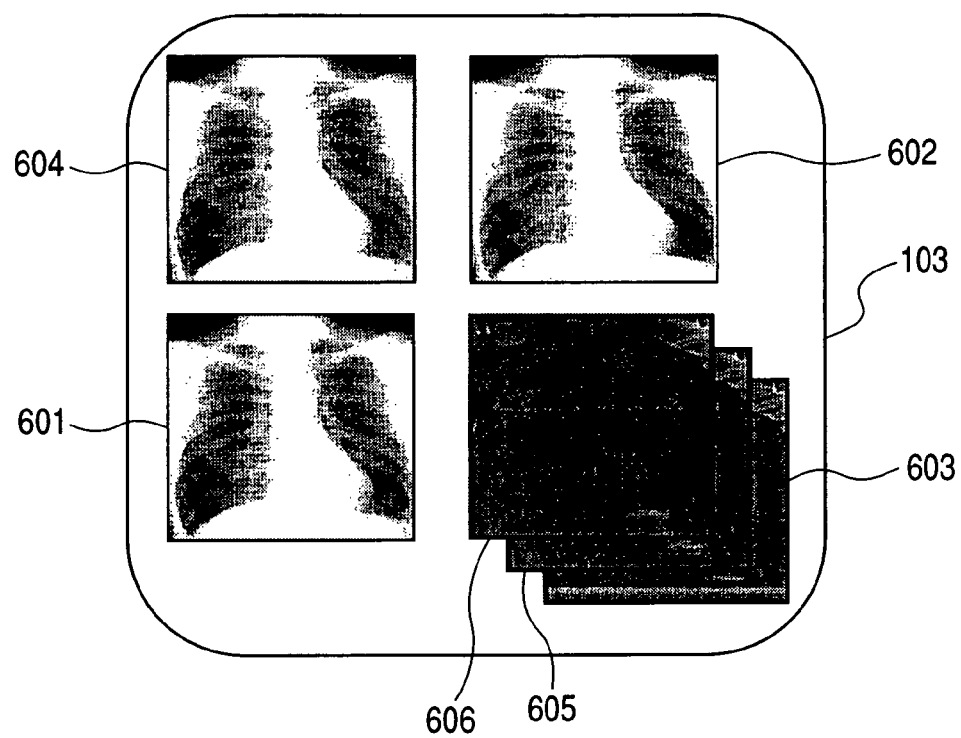
FIG. 14 is a view showing an example of displaying the images shown in FIG. 10 on the display screen.

Moreover, when the classification of the images shown in FIG. 6 is performed in the way of collecting the images of the secondary capture class to be one, the images are displayed as shown in FIG. 14.

Hereupon, the images 603, 605 and 606 are the collected images of the secondary capture class. In this example, although the image 606 is displayed on the top of the secondary capture class images, the display order of the secondary capture class images is not limited to this way.

Next, the image management device judges whether display switching is performed or not (Step S308). Hereupon, the display switching is especially performed when the images of the secondary capture class is classified in the way of associating the images with the images from which the images of the secondary capture class have been generated and the images are displayed in the display form shown in FIG. 13.

When the user gives an instruction of displaying the secondary capture images with a mouse, a keyboard, a pointing device or the like in the display state as shown in FIG. 13, the image display switching unit 212 controls the image reading unit 204 and the image display unit 205 to display the secondary capture images (Step S325).

Figure 15:
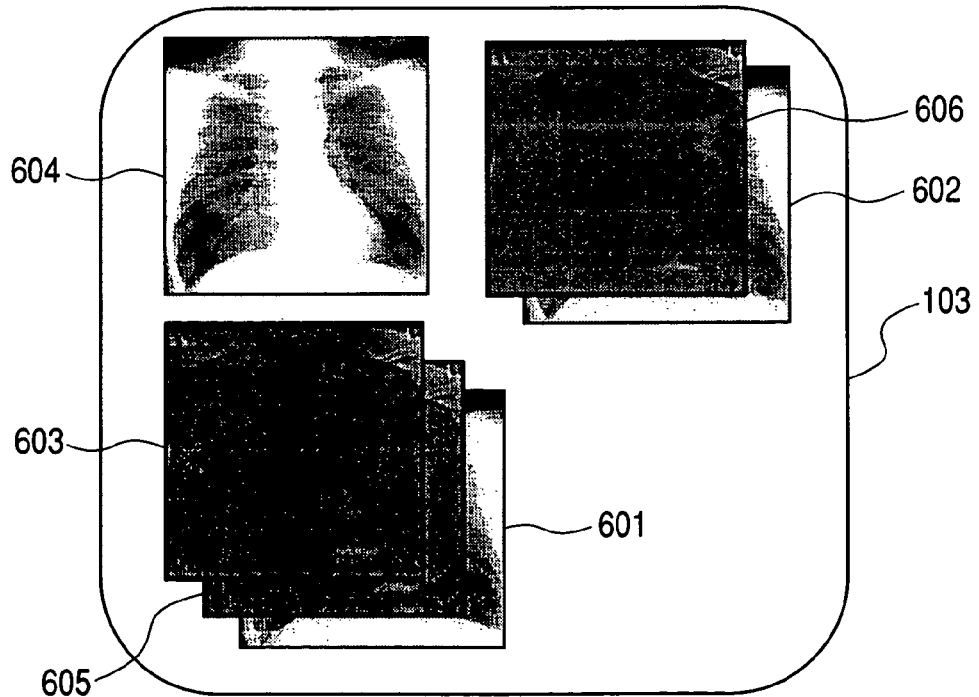
FIG. 15 is a view showing a display when the switching of the display of the images shown in FIG. 13 to a display of secondary capture images is indicated.

An example of the result of having switched the display is shown in FIG. 15. Here, the image 606 is switched from the image 602 to be displayed, and the image 603 is switched from the image 605 to be displayed.

When the image management device judges that no display switching is performed at Step S308, the image management device judges whether there are any image creation instructions (Step S309).

When there are no image creation instructions, the image management device enters the waiting state of an operation of the user as it is (Step S326). When there is an image creation instruction, the image creation instruction unit 206 transfers the parameters for the image processing to the image reading unit 204 (Step S310).

As the images to be created, for example, elapsed difference images, two or more images to be joined to each other to be generated newly as one image, and the like exist. Information required for generating these images, for example, the file names of the two images, image-processing parameters and the like is transferred.

Subsequently, the image reading unit 204 reads the image data specified by the transferred parameters into a memory or a storage area for image processing (Step S311).

After that, the image creation unit 208 performs image processing (Step S312).

Successively, the image creation unit 208 creates image attributes (Step S313). When the image attribute creation has been performed using the images of the same patient at Step S312, unchanged image attributes such as a patient name can be used as they are as the attributes of the secondary capture image to be created newly.

Moreover, the image management device writes into a device type attributes the information that the modality is the SC indicating the secondary capture, and the information capable of being classified by the image processing having generated the secondary capture images as the information peculiar to the secondary capture images. Moreover the image management device registers the file names of the images or the like as the attribute information, which file names or the like are registered as the information by which the file names or the like of the images from which the secondary capture images have been generated can be discriminated.

Next, the image display unit 205 displays the images which the image creation unit 208 has created at Steps S312 and S313 (Step S314).

Subsequently, the image storage unit 209 stores the data of the images which the image creation unit 208 has created at Steps S312 and S313 in the storage medium 102 (Step S315).

Then, the image management device registers the secondary capture image information stored at Step S315 in the database 101 (Step S316). When the image management device registers the information in the database 101, the image management device stores the device types of the secondary capture images, the information specifying the images from which the secondary capture images have been generated, and the like into the database 101 as the attribute information to be used for displaying the images later.

According to the image management device according to such an embodiment, at the time of the creation of the secondary capture images, the information specifying the images from which the secondary capture images have been created are inputted. Thereby, when the images are displayed later, the taken images and the secondary capture images can be displayed in the way of associating them mutually.

Consequently, the occurrence of the state in which taken images and the secondary capture images are confusedly mixed is prevented while the taken images and the secondary capture images can be regularly displayed. Moreover, even if there is a plurality of kinds of secondary captures, by handling those secondary captures in the sate of classifying them by every kind, a defect of the disturbance of interpretation of radiograms of images owing to the existence of different kinds of secondary capture images can be avoided.

Moreover, since the image classification methods and the display modes can be switched, it is possible to compare the secondary capture images with each other, or to switch the taken images and the secondary capture images from each other to display them. Consequently, the image management device can contributes to the improvement of the diagnosis efficiency of a doctor and the accuracy thereof.

Incidentally, in the embodiment described above, the image processing is executed on the side of the image storage device 105, but the image processing may be executed on the side of the image display device 103 by providing a CPU and a ROM to the image display device 103.

Figure 19:
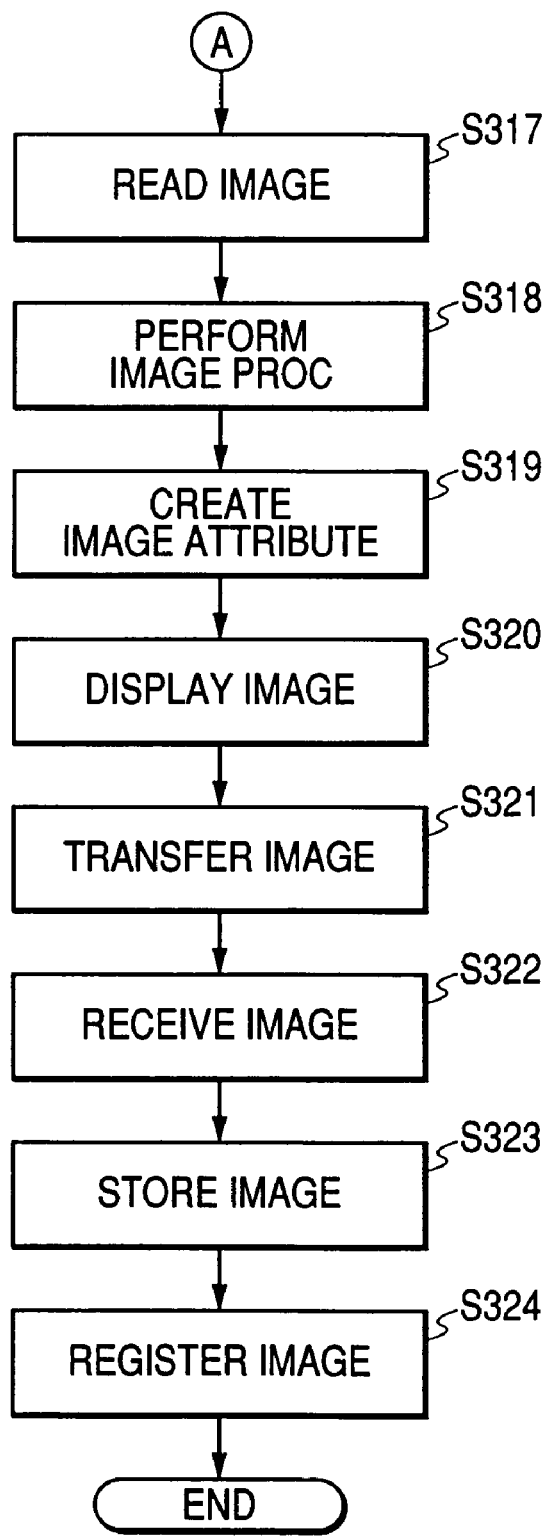
FIG. 19 is a flowchart showing a processing operation in a case where image processing is performed on the side of an image display device 103.

In this case, the processing shown in FIG. 3A is the same as that of the embodiment described above, but the processing shown in FIG. 3B is omitted, and the processing shown in FIG. 19 is executed on the side of the image display device 103. However, as for the functional blocks shown in FIG. 2, it is supposed to use the similar ones to those of the embodiment described above.

In case of the execution on the side of the image display device 103, when image creation instruction is issued (Step S309), the image reading unit 204 reads image data onto the memory or the storage area formed on the image display device 103 for image processing of image data (Step S317). However, the image data has already been read for the image display at Step S307, the processing at Step S317 may be omitted.

After that, the image creation unit 208 performs the image processing (Step S318).

Successively, the image creation unit 208 creates image attributes (Step S319).

Next, the image display unit 205 displays the images created at Steps S318 and S319 by the image creation unit 208 (Step S320). Successively, the data of the created images is transferred from the image display device 103 to the image storage device 105 (Step S321), and the data is received by the image storage device 105 (Step S322). As the transfer method, for example, a transfer method using a transfer protocol regulated by DICOM standard can be cited, and the transfer may be performed using a well-known general method.

Next, the image storage unit 209 stores the data of the images created by the image creation unit 208 at Steps S318 and S319 into the storage medium 102 (Step S323). Then, the secondary capture image information stored at Step S323 is registered into the database 101 (Step S324).

Incidentally, about the latest test, even when the instruction of displaying the secondary capture images is received, the display of the secondary capture images may be omitted. Moreover, even if an instruction of displaying the secondary capture images is received, the tests which do not include the secondary capture images may be omitted.

Second Embodiment

The first embodiment mainly concerns the example in which the images of the secondary capture class are generated from the images of the different tests such as elapsed difference images. The second embodiment concerns the case where two or more images in the same test are joined to each other to be one image and the joined image is made to be a newly generated digital image.

Figure 16:
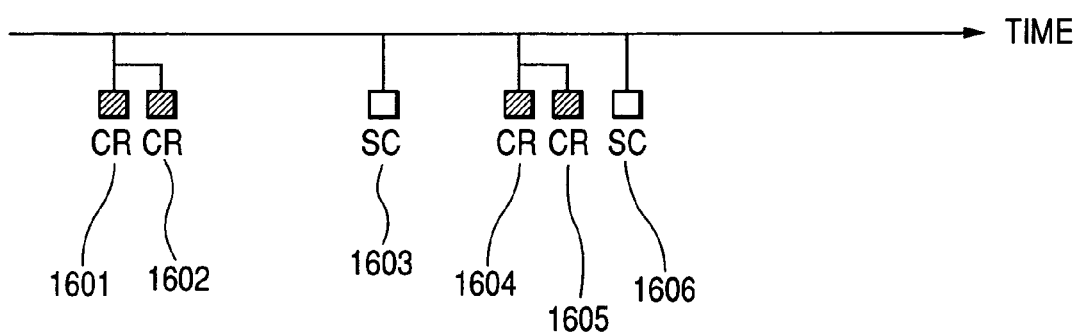
FIG. 16 is a conceptual diagram showing a case where secondary capture images are created from one or more images in the same test.
Figure 17:
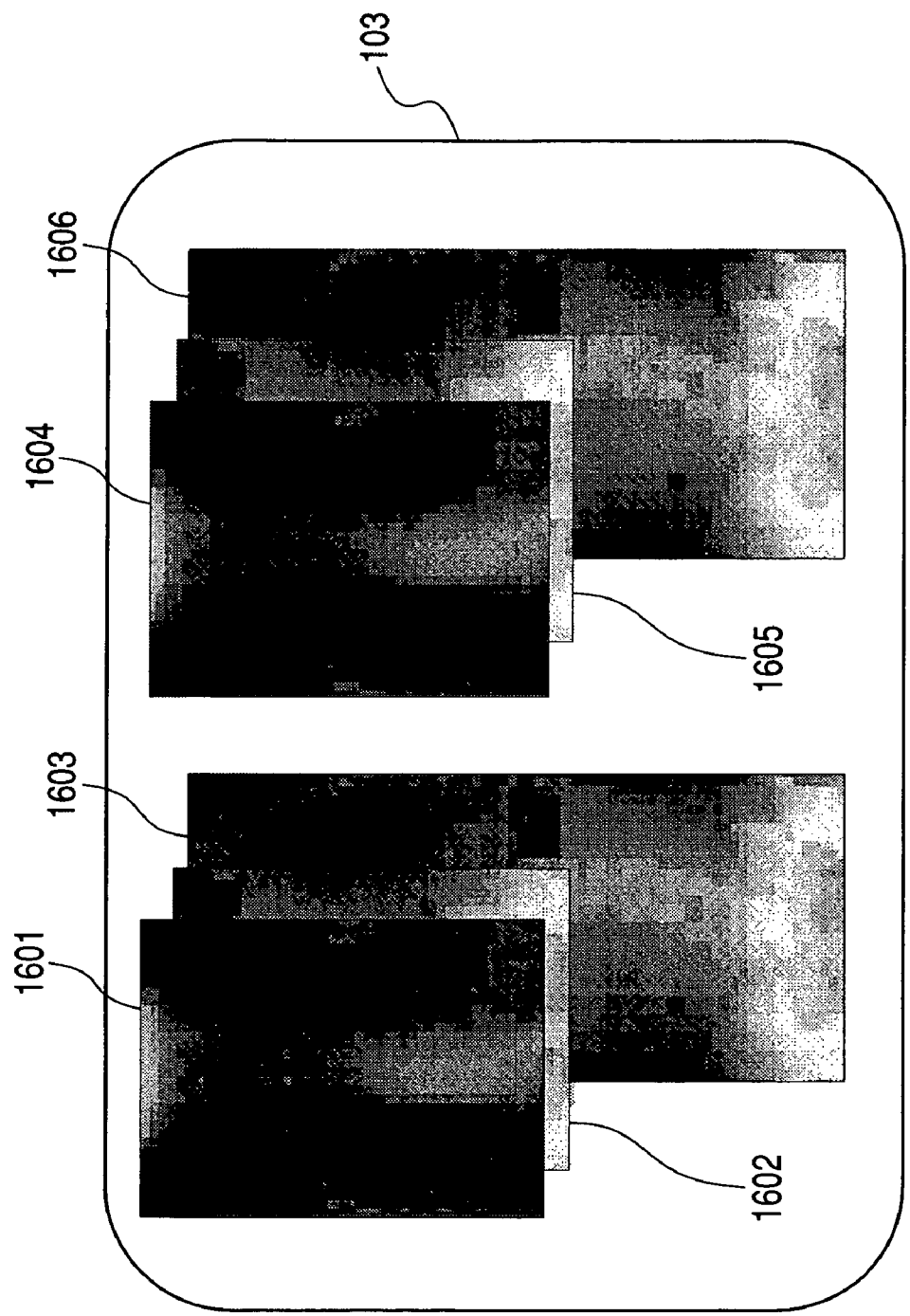
FIG. 17 is a view showing an example of displaying the images of FIG. 16 on the display screen.

For example, as shown in FIG. 16, when images 1601 and 1602 of the CR class are joined together and thereby an image 1603 of the secondary capture class is newly generated, as shown in FIG. 17, the images of the secondary capture class are classified in the images of the class being the generation origin.

Figure 18:
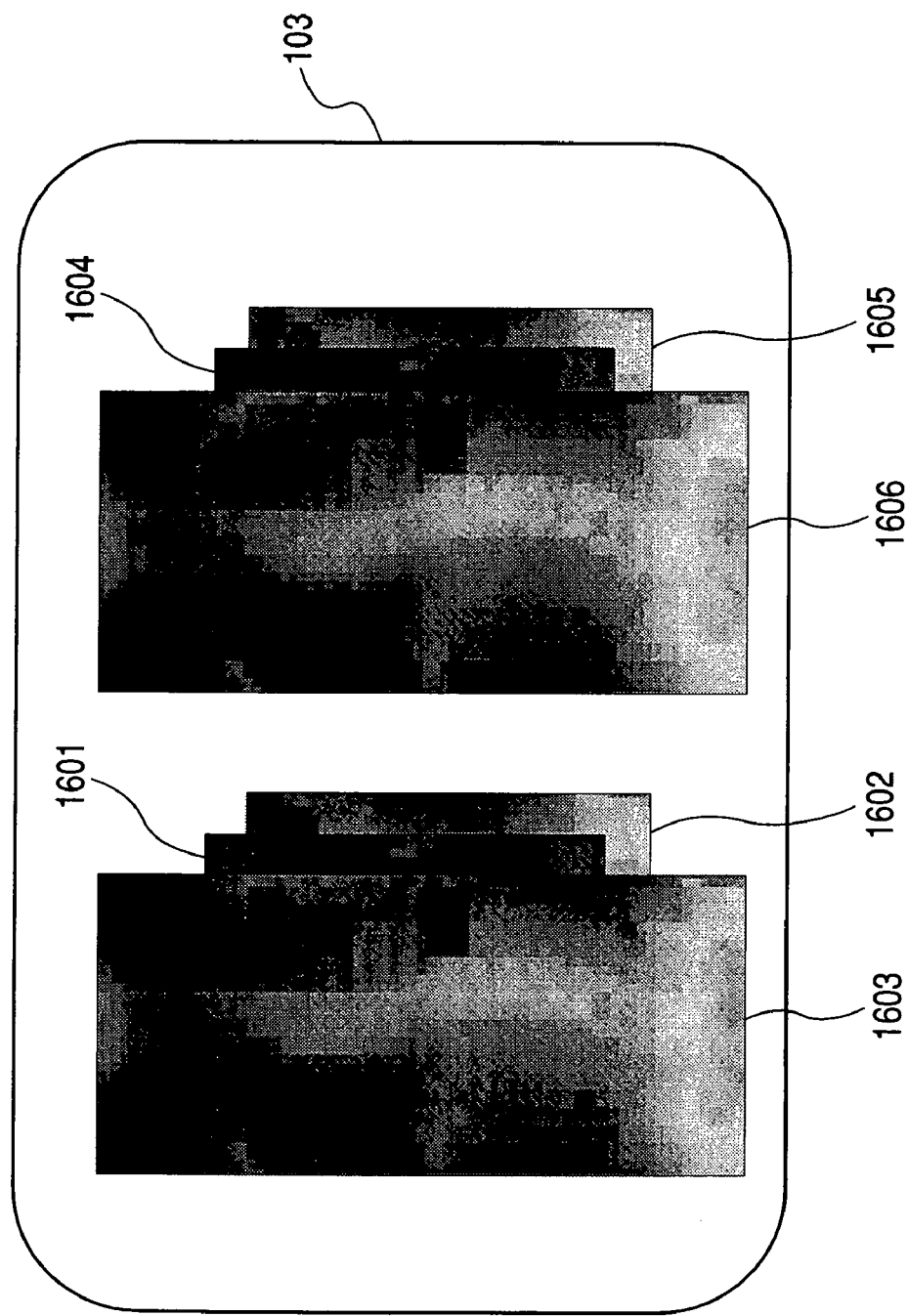
FIG. 18 is a view showing a display when a instruction of switching the display of the images shown in FIG. 17 to a display of secondary capture images is issued.

On the other hand, when the display switching at Step S308 is performed, as shown in FIG. 18, the secondary capture images 1603 and 1606 are displayed.

Third Embodiment

The third embodiment is configured so that a display switching step of Step S308 can give a switching instruction about an image classification, and so that the image display switching unit 212 performs image classification switching to display images.

Incidentally, the embodiments of the present invention can be realized by, for example, a computer executing programs. Moreover, means for supplying the programs to the computer, for example, a recording medium, in which such programs are recorded, such as a CD-ROM capable of being read by a computer, or a transmission medium such as the Internet transmitting such programs can be also applied as an embodiment of the present invention. Moreover, the programs mentioned above can be also applied as an embodiment of the present invention. The programs, the recording medium, the transmission medium and the program products are included in the scope of the present invention.

This application claims priority from Japanese Patent Application No. 2004-200920 filed on Jul. 7, 2004, which is hereby incorporated by reference herein.

What is claimed is:

1. An image management device, comprising:
    an attribute judgment unit judging whether each of the images is a processed image generated by performing image processing of a taken image or whether each of the images is a taken image based on attribute information of the image, wherein the attribute information includes test information;
    switching instruction unit instructing switching of first classification way to classifying a plurality of the processed images into one group, second classification way to classifying the processed image and the taken image in the same test into one group, and third classification way to classifying the processed image and the taken image in accordance with the order of the test dates;
    a classification unit classifying the images based on a judgment result of said attribute judgment unit and the instruction of said switching instruction unit;
    an image display unit displaying the classified images with the order of the test dates when said switching instruction unit instructs the third classification way, displaying one image in the group by the group when said switching instruction unit instructs the first classification way or the second classification way, omitting the display of the processed image when the test date is the latest, and omitting the display of the images of the test when the images do not include the processed image; and
    a switching unit switching the display of the image displayed by said display unit to the display of the other image in the same group when the classified images are displayed by the group.

2. An image management device according to claim 1, wherein said classification means classifies an image which is judged to be the processed image in a way of associating the image with the taken image related to the image.

3. An image management device according to claim 1, wherein said classification unit classifies an image judged to be the processed image in a way of associating the image with an image judged to be the processed image.

4. An image management device according to claim 1, wherein the processed image is an image acquired by performing difference processing between a plurality of the taken images acquired by radiographing the same subject at different time points.

5. An image management device according to claim 1, wherein the processed image is an image acquired by performing image processing of joining a plurality of the taken images to each other, the taken images acquired by radiographing different parts of the same subject.

6. An image management device according to claim 1, wherein said attribute judgment unit judges whether an image is the processed image or not based on whether a class attribute included in the attribute information of the image is a secondary capture class or not.

7. An image management method being executed by an image management device, comprising:

an attribute judgment step of judging whether each of images is a processed image generated by performing image processing of a taken image or whether each of the images is the taken image based on attribute information of the image, wherein the attribute information includes test information;

a switching instruction step instructing switching of first classification way to classifying a plurality of the processed images into one group, second classification way to classifying the processed image and the taken image in the same test into one group, and third classification way to classifying the processed image and the taken image in accordance with the order of the test dates;

a classification step of classifying the images based on a judgment result at the attribute judgment step and the instruction of said switching instruction step;

an image display step of displaying the classified images with the order of the test dates when said switching instruction step instructs the third classification way, displaying one image in the group by the group when said switching instruction step instructs the first classification way or the second classification way, omitting the display of the processed image when the test date is the latest, and omitting the display of the images of the test when the images do not include the processed image; and a switching step of switching the display of the image displayed in said display step to the display of the other image in the same group when the classified images are displayed by the group.

8. An image management method according to claim 7, wherein at said classification step, an image judged to be the processed image is classified in a way of being associated with the taken image related to the image.

9. An image management method according to claim 7, wherein at said classification step, an image judged to be the processed image is classified in a way of being associated with another image judged to be the processed image.

* * * * *